United States Patent
Williams et al.

(10) Patent No.: US 11,633,522 B1
(45) Date of Patent: *Apr. 25, 2023

(54) MALLEABLE, CRYOPRESERVED OSTEOGENIC COMPOSITIONS WITH VIABLE CELLS

(71) Applicant: NuVasive, Inc., San Diego, CA (US)

(72) Inventors: Gregory Williams, San Diego, CA (US); Erik Erbe, San Diego, CA (US); Susan Lynn Riley, San Diego, CA (US); Timothy Moseley, Solana Beach, CA (US); Ali Ismailoglu, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 136 days.

This patent is subject to a terminal disclaimer.

(21) Appl. No.: 16/995,128

(22) Filed: Aug. 17, 2020

Related U.S. Application Data

(63) Continuation of application No. 14/066,589, filed on Oct. 29, 2013, now Pat. No. 10,780,197.

(60) Provisional application No. 61/719,868, filed on Oct. 29, 2012.

(51) Int. Cl.
    *A61L 27/36* (2006.01)

(52) U.S. Cl.
    CPC .................. *A61L 27/365* (2013.01)

(58) Field of Classification Search
    None
    See application file for complete search history.

(56) References Cited

U.S. PATENT DOCUMENTS

| | | | |
|---|---|---|---|
| 4,065,816 A | 1/1978 | Sawyer | |
| 4,108,161 A | 8/1978 | Samuels et al. | |
| 4,802,853 A | 2/1989 | Krasner | |
| 5,071,741 A * | 12/1991 | Brockbank | A01N 1/0221 435/1.3 |
| 5,118,512 A | 6/1992 | O'Leary | |
| 5,345,746 A | 9/1994 | Franchi | |
| 5,385,229 A | 1/1995 | Bittmann et al. | |
| 5,480,424 A | 1/1996 | Cox | |
| 5,531,791 A | 7/1996 | Wolfinbarger, Jr. | |
| 5,676,146 A | 10/1997 | Scarborough | |
| 5,697,383 A | 12/1997 | Manders et al. | |
| 5,788,941 A | 8/1998 | Dalmasso | |
| 5,910,315 A | 6/1999 | Stevenson et al. | |
| 5,989,498 A | 11/1999 | Odland | |
| 6,024,735 A | 2/2000 | Wolfinbarger, Jr. | |
| 6,083,690 A | 7/2000 | Harris et al. | |
| 6,189,537 B1 | 2/2001 | Wolfinbarger, Jr. | |
| 6,203,755 B1 | 3/2001 | Odland | |
| 6,254,635 B1 | 7/2001 | Schroeder et al. | |
| 6,293,970 B1 | 9/2001 | Wolfinbarger, Jr. et al. | |
| 6,294,187 B1 | 9/2001 | Boyce et al. | |
| 6,295,187 B1 | 9/2001 | Pinarbasi | |
| 6,311,690 B1 | 11/2001 | Jefferies | |
| 6,432,436 B1 | 8/2002 | Gertzman et al. | |
| 6,652,818 B1 | 11/2003 | Mills et al. | |
| 6,652,872 B2 | 11/2003 | Nevo | |
| 6,739,112 B1 | 5/2004 | Marino | |
| 7,162,850 B2 | 1/2007 | Marino et al. | |
| 7,892,724 B2 | 2/2011 | Shimko et al. | |
| 8,460,860 B2 | 6/2013 | Williams | |
| 9,352,003 B1 | 5/2016 | Semler | |
| 9,687,348 B2 | 6/2017 | Vunjak-Novakovic et al. | |
| 2001/0039458 A1 | 11/2001 | Boyer, II et al. | |
| 2002/0018796 A1 | 2/2002 | Wironen | |
| 2004/0230309 A1 | 11/2004 | DiMauro et al. | |
| 2006/0083769 A1 | 4/2006 | Kumar et al. | |
| 2006/0240064 A9 | 10/2006 | Hunter et al. | |
| 2007/0260326 A1 | 11/2007 | Williams et al. | |
| 2008/0262633 A1 | 10/2008 | Williams et al. | |

FOREIGN PATENT DOCUMENTS

| | | |
|---|---|---|
| WO | 1997039104 A1 | 10/1997 |
| WO | 2002032474 A1 | 4/2002 |
| WO | 2007133451 A1 | 11/2007 |
| WO | 2009134815 A1 | 11/2009 |

OTHER PUBLICATIONS

Alberts et al., "Chapter 23 Specialized Tissues, Stem Cells and Tissue Renewal", Molecular Biology of the Cell, 5th Edition, Garland Science, 2008, p. 1457.

An et al., "Comparison between allograft plus demineralized bone matrix versus autograft in anterior cervical fusion| A prospective multicenter study", SPINE, 1995, pp. 2211-2216, 20, No. 20.

Caplan, "What's in a Name?", Tissue Engineering, 2010, pp. 2415-2417, 16, No. 8.

Cook et al., "In vivo evaluation of demineralized bone matrix as a bone graft substitute for posterior spinal fusion", SPINE, 1995, pp. 877-886, 20, No. 8.

(Continued)

*Primary Examiner* — Jessica Worsham
(74) *Attorney, Agent, or Firm* — Hoffman Warnick LLC

(57) ABSTRACT

A bone graft composition comprising a viable, osteogenic cellular material combined with a viscous cryoprotectant that includes a penetrating cryoprotective agent and a non-penetrating cryoprotective agent. The viscosity of the cryoprotectant is such that the composition is malleable, cohesive and capable of being formed into desired shapes.

14 Claims, No Drawings

(56) References Cited

OTHER PUBLICATIONS

Gazdag et al., "Alternatives to autogenous bone graft: Efficacy and indications", J Am Acad Orthop Surg, 1995, pp. 1-8, 3, No. 1.

Ginis et al., "Evaluation of bone marrow-derived mesenchymal stem cells after cryopreservation and hypothermic storage in clinically safe medium", Tissue Engineering Part C: Methods, 2012, pp. 453-463, 18, No. 6.

International Search Report for PCT/US2007/010589, ISA, dated Sep. 22, 2007, pp. 1.

International Search Report for PCT/US2009/041999, ISA, dated Jun. 8, 2009, pp. 2.

Lambrecht et al., "Human osteoclast-like cells in primary culture", Clinical Anatomy, 1996, pp. 41-45, 9, No. 1.

Laursen et al., "Optimal handling of fresh cancellous bone graft. Different peroperative storing techniques evaluated by in vitro osteo-blast-like cell metabolism", Acta Orthop Scand, 2003, pp. 490-496, 74, No. 4.

Mayer, "Properties of human trabecular bone cells from elderly women: Implications for cell-based bone engraftment" Cells Tissues Organs, 2004, pp. 57-67, 177, No. 2.

McAllister et al., "Histologic evaluation of a stem cell-based sinus-augmentation procedure", J Periodontal, 2009, pp. 679-686, 80, No. 4.

Robey et al., "Human bone cells in vitro", Calcif Tissue Int, 1985, pp. 453-460, 37, No. 5.

Sakaguchi et al., "Suspended cells from trabecular bone by collagenase digestion become virtually identical to mesenchymal stem cells obtained from marrow aspirates", Blood, 2004, pp. 2728-2735, 104, No. 9.

Written Opinion for PCT/US2007/010589, ISA, dated Sep. 22, 2007, pp. 3.

Written Opinion for PCT/US2009/041999, ISA, dated Jun. 8, 2009, pp. 5.

Kylmaoja et al., "Osteoclasts and remodeling based bone formation", Current Stem Cell Research & Therapy, 2016, Abstract, 11, No. 8.

Matter et al., "Biomechanical examinations of cancellous bone concerning the influence of duration and temperature of cryopreservation", J Biomed Mater Res, 2001, pp. 40-44, 55, No. 1.

Oh et al., "A new bone banking technique to maintain osteoblast viability in frozen human iliac cancellous bone", Cryobiology, 2002, pp. 279-287, 44, No. 3.

Van der Donk et al., "Rinsing morselized allografts improves bone and tissue ingrowth", Clinical Orthopaedics and Related Research, 2003, pp. 302-310, No. 408.

\* cited by examiner

MALLEABLE, CRYOPRESERVED OSTEOGENIC COMPOSITIONS WITH VIABLE CELLS

CROSS REFERENCE TO RELATED APPLICATIONS

This application is a continuation of U.S. patent application Ser. No. 14/066,589 filed Oct. 29, 2013, which claims the benefit of priority of U.S. provisional application No. 61/719,868 filed on Oct. 29, 2012, each of which are hereby incorporated by reference herein as if set forth herein in their entireties.

FIELD

This application relates to a bone graft composition, useful in surgical applications, comprising viable cellular material combined with a viscous cryoprotectant.

SUMMARY

According to an exemplary embodiment, the bone graft composition comprises a viable, osteogenic cellular material combined with a viscous cryoprotectant that includes a penetrating cryoprotective agent and a non-penetrating cryoprotective agent. According to an exemplary embodiment, the viscosity of the cryoprotectant is such that the composition is malleable, cohesive and capable of being formed into desired shapes. According to another exemplary embodiment, the osteogenic cellular material includes viable mesenchymal stem cells. According to yet another embodiment, the osteogenic composition includes at least one of demineralized cortical bone, demineralized cancellous bone, growth factors, bone marrow, BMP-2, BMP-4, BMP-7, or a combination thereof. The characteristics of viscous cryoprotectant allow the composition to be frozen and subsequently thawed and implanted into a patient in need thereof while preserving the viability of the mesenchymal stem cells in the composition.

According to one aspect, the viable osteogenic cellular material is autogenous bone matrix having a population of endogenous osteopotent and/or osteogenic cells. According to another aspect, the viable osteogenic cellular material is allogeneic bone matrix having a population of endogenous osteopotent and/or osteogenic cells. The viable osteogenic cellular material may be substantially depleted of blood cells. The cellular material may include mesenchymal stem cells derived from bone marrow, adipose tissue, muscle, synovium, synovial fluid, dental pulp and/or umbilical cord origin.

According to another aspect, non-penetrating cryoprotective agent is one of alginate, hyaluronic acid, hydroxyethyl starch, methylcellulose, carboxymethylcellulose, hydroxymethylcellulose, polyvinylpyrrolidone, polyethylene glycol, chitosan, glycerol, or a combination thereof. The penetrating cryoprotective agent is one of dimethyl sulfoxide, glycerol, propylene glycol, ethylene glycol, propanediol, or a combination thereof. According to another exemplary embodiment, the bone graft composition further comprises a scaffold material. For example, the scaffold material is one of non-demineralized, partially demineralized and demineralized cortical bone matrix; nondemineralized, partially demineralized and demineralized cancellous bone matrix; hydroxyapatite, tri-calcium phosphate, calcium sulfate, collagen or a combination thereof.

According to yet another exemplary embodiment, the viable osteogenic cellular material comprises particles cohesively bound by the viscous cryoprotectant. Alternatively, the viable osteogenic cellular material may be coated or encapsulated by the viscous cryoprotectant.

DETAILED DESCRIPTION

Aspects of the invention are disclosed in the following description. Alternate embodiments may be devised without departing from the spirit or the scope of the invention. Additionally, well-known elements of the invention will not be described in detail or omitted so as not to obscure the relevant details of the invention.

Example 1

Viscous cryoprotectant compositions were created for subsequent combination with tissue components. A 10% (v/v) dimethyl sulfoxide (DMSO) solution was created in an isotonic, pH neutral solution with acetate and gluconate buffers. Pre-weighed quantities of sodium alginate were dissolved in the 10% DMSO solution to achieve concentrations of 1%-4% (w/v) alginate. Alginates had been pre-selected with a Brookfield viscosity specification in the range of 100-10,000 cps when tested at 2% in water at 25 degrees C.

Relative apparent viscosities were determined for each of the final cryoprotectant solutions and ranked such that 7>6>5>4>3>2>1, as shown in Table 1.

TABLE 1

| Cryoprotectant Solution ID | Alginate Concentration | Alginate Viscosity Spec | Relative Viscosity |
|---|---|---|---|
| A | 1% | 100-300 cps | 1 |
| B | 2% | 100-300 cps | 2 |
| C | 4% | 100-300 cps | 5 |
| D | 1% | >2000 cps | 3 |
| E | 1.5% | >2000 cps | 4 |
| F | 2% | >2000 cps | 6 |
| G | 4% | >2000 cps | 7 |

Example 2

Viable cellular cancellous bone was ground and sieved to 425-2000 μm. Cortical bone was ground, sieved to 125-1000 μm, and demineralized to <8% residual calcium content to create hydrated demineralized bone matrix (DBM). Tissue components were mixed in cancellous:DBM volume ratios of 10:3-2:1. Tissue mixtures were combined with cryoprotectants essentially identical to those of Example 1 at a cancellous:cryoprotectant volume ratio of 5:1. Tissue and cryoprotectant components were mixed to form malleable compositions with variously satisfactory cohesiveness and formability, as shown in Table 2.

TABLE 2

| Cancellous:DBM (v:v) | Cryoprotectant Solution ID | Cancellous:Cryo (v:v) | Cohesiveness/ Formability |
|---|---|---|---|
| 10:3 | D | 5:1 | poor |
| 10:3 | E | 5:1 | poor |
| 10:3 | C | 5:1 | fair |
| 10:3 | F | 5:1 | fair |
| 2:1 | F | 5:1 | fair |
| 2:1 | G | 5:1 | good |

TABLE 2-continued

| Cancellous:DBM (v:v) | Cryoprotectant Solution ID | Cancellous:Cryo (v:v) | Cohesiveness/ Formability |
|---|---|---|---|

Example 3

Viable cellular cancellous bone was ground and sieved to 425-2000 μm. Cortical bone was ground, sieved to 100-710 μm, demineralized to <8% residual calcium content, and lyophilized to create lyophilized DBM. Tissue components were mixed at a cancellous:DBM volume ratio of 2:1. The tissue mixture was combined with cryoprotectants essentially identical to those of Example 1 at cancellous:cryoprotectant volume ratios of 10:3-5:2. Tissue and cryoprotectant components were mixes and evaluated for cohesiveness and formability; the results are summarized in Table 3.

TABLE 3

| Cancellous:DBM (v:v) | Cryoprotectant Solution ID | Cancellous:Cryo (v:v) | Cohesiveness/ Formability |
|---|---|---|---|
| 2:1 | G | 10:3 | fair |
| 2:1 | G | 5:2 | good |

Example 4

Viable cellular cancellous bone was ground and sieved to 425-2000 μm. Cortical bone was ground, sieved to 100-710 μm, demineralized to <8% residual calcium content, and lyophilized to create lyophilized DBM. Lyophilized DBM was subsequently rehydrated in an isotonic, neutral pH solution and mixed with cancellous bone at a cancellous:DBM volume ratio of 10:7. The tissue mixture was combined with a cryoprotectant essentially identical to Solution G in Example 1 at a cancellous:cryoprotectant volume ratio of 10:3. Tissue and cryoprotectant components were mixed and evaluated for cohesiveness and formability; the results are summarized in Table 4.

TABLE 4

| Cancellous:DBM (v:v) | Cryoprotectant Solution ID | Cancellous:Cryo (v:v) | Cohesiveness/ Formability |
|---|---|---|---|
| 10:7 | G | 10:3 | good |

Example 5

Viscous cryoprotectant compositions were created for subsequent combination with tissue components. Pre-weighed quantities of sodium alginate having a Brookfield viscosity specification of >2000 cps when tested at 2% in water at 25 degrees C. were suspended in measured volumes of DMSO. Measured quantities of an isotonic, pH neutral solution with acetate and gluconate buffers were mixed with the alginate/DMSO suspensions to create substantially homogeneous cryoprotectant solutions with final DMSO concentrations of 5%-10% (v/v) and alginate concentrations of 2%-4% (w/v).

Relative apparent viscosities were determined for each of the final cryoprotectant solutions and ranked such that 7>6>5>4>3>2>1, as shown in Table 5. IDC-2531

TABLE 5

| Cryoprotectant Solution ID | Alginate Concentration | DMSO Concentration | Relative Viscosity |
|---|---|---|---|
| H | 2% | 5% | 1 |
| I | 2.5% | 5% | 2 |
| J | 3% | 5% | 4 |
| K | 4% | 5% | 6 |
| L | 2% | 10% | 3 |
| M | 2.5% | 10% | 5 |
| N | 3% | 10% | 6 |
| O | 4% | 10% | 7 |

Example 6

Viable cellular cancellous bone was ground and sieved to 425-2000 μm. Cortical bone was ground, sieved to 125-1000 μm, and demineralized to <8% residual calcium content to create hydrated DBM. Tissue components were mixed at cancellous:DBM volume ratios of 5:1-2:1. Tissue mixtures were combined with a cryoprotectant essentially identical to Solution 0 of Example 5 with the addition of 2% (w/v) human serum albumin at cancellous:cryoprotectant volume ratios of 5:1-4:1. Tissue and cryoprotectant components were mixed and evaluated for cohesiveness and formability, the results of which are summarized in Table 6.

TABLE 6

| Cancellous:DBM (v:v) | Cancellous:Cryo (v:v) | Cohesiveness/ Formability |
|---|---|---|
| 5:1 | 5:1 | fair |
| 4:1 | 5:1 | fair |
| 3:1 | 5:1 | good |
| 2:1 | 5:1 | good |
| 5:1 | 4:1 | fair |
| 4:1 | 4:1 | fair |
| 3:1 | 4:1 | good |
| 2:1 | 4:1 | better |

Example 7

Viable cellular cancellous bone was ground and sieved to 425-2000 μm. Cortical bone was ground, sieved to 125-1000 μm, and demineralized to <8% residual calcium content to create hydrated DBM. Tissue components were mixed at a cancellous:DBM volume ratio of 2:1. Cryoprotectant solutions were created consisting of DMSO at 5%-10% (v/v), human serum albumin at 0%-2% (w/v), and alginate at 4% (w/v) in an isotonic, neutral pH parenteral solution. Tissue mixtures were combined with cryoprotectants at a cancellous:cryoprotectant volume ratio of 4:1. Tissue and cryoprotectant components were mixed to create substantially homogeneous malleable compositions. Compositions were frozen to −80±5° C. to cryopreserve tissue components and viable cells.

Compositions were subsequently thawed and tested for cell viability (% viable cells) and cell concentrations (cells per cc of tissue). Compositions were rinsed immediately after thawing with phosphate buffered saline to dilute and decant the viscous cryoprotectant solutions. The remaining tissue components were treated with 3 mg/ml collagenase in phosphate buffered saline at 37° C. to release cells off bone matrix for counting. Released cells were washed and resuspended in Dulbecco's Modified Eagle Medium with 10% fetal bovine serum and then stained with Trypan blue. Live (negative staining) and dead (positive staining) cells were counted with the aid of a hemocytometer and microscope. The results are summarized in Table 7.

TABLE 7

| Composition ID | DMSO Concentration (v/v) | Human Serum Albumin Concentration (w/v) | Avg. Cell Viability | Avg. Cell Count (cells/cc) |
|---|---|---|---|---|
| A | 10% | 0% | 76.4% | 4,154,500 |
| B | 7.5% | 0% | 74.7% | 3,787,000 |
| C | 5% | 0% | 77.2% | 4,399,500 |
| D | 10% | 2% | 76.8% | 4,301,500 |
| E | 7.5% | 2% | 80.6% | 4,063,500 |
| F | 5% | 2% | 77.1% | 3,279,500 |

Example 8

Viable cellular cancellous bone was ground and sieved to 425-2000 μm. Cortical bone was ground, sieved to 125-1000 μm, and demineralized to <8% residual calcium content to create hydrated DBM. Tissue components were mixed at cancellous:DBM volume ratios of 5:2 to 5:3. Cryoprotectant solutions were created consisting of DMSO at 10% (v/v), human serum albumin at 2% (w/v), and alginate at 6% (w/v) in an isotonic, neutral pH parenteral solution. Alginates in this example had molecular weights (MW) between 50,000 and 150.000 g/mol. Tissue mixtures were combined with cryoprotectants at cancellous:cryoprotectant volume ratios of 5:2 to 2:1. Tissue and cryoprotectant components were mixed to create substantially homogeneous malleable compositions. Compositions were frozen to −80±5° C. to cryopreserve tissue components and viable cells.

Compositions were subsequently thawed and tested for cell viability (% viable cells), cell concentrations (cells per cc of tissue), and osteogenic potential. Compositions were rinsed immediately after thawing with phosphate buffered saline to dilute and decant the viscous cryoprotectant solutions. The remaining tissue components were treated with 3 mg/ml collagenase in phosphate buffered saline at 37° C. to release cells off bone matrix for counting. Released cells were washed and resuspended in Dulbecco's Modified Eagle Medium with 10% fetal bovine serum and then stained with Trypan blue. Live (negative staining) and dead (positive staining) cells were counted with the aid of a hemocytometer and microscope. Cells were plated and cultured in expansion medium through one passage. Cells were then switched into osteogenic medium and subsequently stained for the presence of the bone mineralization marker alkaline phosphatase. The results are summarized in Table 8. IDC-28,T 1 Table 8:

TABLE 8

| Composition ID | Alginate Lot ID | Cancellous:Cryo (v:v) | Avg. Cell Viability | Avg. Cell Count (cells/cc) | Alk. Phos. Staining |
|---|---|---|---|---|---|
| A | 1 | 5:2 | 85.5% | 2,761,500 | Positive |
| B | 1 | 2:1 | 86.3% | 2,732,750 | Positive |
| C | 2 | 5:2 | 87.8% | 2,824,750 | Positive |
| D | 2 | 2:1 | 89.0% | 2,767,000 | Positive |

What is claimed is:

1. A bone graft composition comprising:
   bone particles containing viable osteogenic cellular material native to the bone particles;
   a viscous cryoprotectant comprising at least one penetrating cryoprotective agent and at least one non-penetrating cryoprotective agent, wherein the at least one non-penetrating cryoprotective agent comprises alginate,
   wherein the viscous cryoprotectant comprises a concentration of alginate of 4% to 6%; and
   a demineralized bone matrix,
   wherein a volume ratio of the bone particles to the demineralized bone matrix is in a range from 5:2 to 53, and wherein the bone graft composition is homogenous and malleable,
   wherein a second volume ratio of the bone particles to the viscous cryoprotectant is from 5:2 to 2:1, and
   wherein at least seventy percent of the viable osteogenic cellular material is viable after storage in the viscous cryoprotectant at −80 degrees Celsius or lower for a period of fourteen days.

2. The bone graft composition of claim 1, wherein the bone particles are from viable cancellous bone, and the demineralized bone matrix is from cortical bone.

3. The bone graft composition of claim 1, wherein the bone particles are cohesively bounded by the viscous cryoprotectant.

4. The bone graft composition of claim 1, wherein the bone particles are coated or encapsulated by the viscous cryoprotectant.

5. The bone graft composition of claim 1, wherein a viscosity of the viscous cryoprotectant is higher than 2000 centipoises (cps).

6. The bone graft composition of claim 1, wherein the non-penetrating cryoprotective agent further comprises one or more of hyaluronic acid, hydroxyethyl starch, methylcellulose, carboxymethylcellulose, hydroxymethylcellulose, polyvinylpyrrolidone, polyethylene glycol, chitosan, and glycerol.

7. The bone graft composition of claim 1, wherein the penetrating cryoprotective agent is one of dimethyl sulfoxide, glycerol, propylene glycol, ethylene glycol, propanediol, or a combination thereof.

8. A method of preserving viability of a bone graft material, the method comprising:
   combining viable bone graft material with a demineralized bone matrix, wherein a volume ratio of the viable bone graft material to the demineralized bone matrix ranges from 5:2 to 5:3 and wherein the viable bone graft material contains viable osteogenic cells inherent thereto; and
   combining the viable bone graft material and the demineralized bone matrix with a viscous cryoprotectant into a homogenous composition for preserving the viability of the viable bone graft material, wherein the viscous cryoprotectant includes at least one non-penetrating cryoprotective agent and at least one penetrating cryoprotective agent, wherein the at least one non-penetrating cryoprotective agent comprises alginate,
   wherein a second volume ratio of the viable bone graft material to the viscous cryoprotectant is from 5:2 to 2:1,
   wherein the viscous cryoprotectant comprises a concentration of alginate of 4% to 6%, and wherein at least seventy percent of the viable osteogenic cellular material is viable after storage in the viscous cryoprotectant at −80 degrees Celsius or lower for a period of fourteen days.

9. The method claim 8, wherein the viable bone graft material is from viable cancellous bone, and the demineralized bone matrix is from viable cortical bone.

10. The method claim of 8, wherein the viable bone graft material is from viable cortical bone, and the demineralized bone matrix is from viable cancellous bone.

11. The method claim 8, wherein the viable bone graft material is cohesively bounded by the viscous cryoprotectant.

12. The method of claim 8, wherein a viscosity of the viscous cryoprotectant is higher than 2000 centipoises (cps).

13. The method claim of 8, wherein the non-penetrating cryoprotective agent further comprises one or more of hyaluronic acid, hydroxyethyl starch, methylcellulose, carboxymethylcellulose, hydroxymethylcellulose, polyvinylpyrrolidone, polyethylene glycol, chitosan, and glycerol.

14. The method claim of 8, wherein the penetrating cryoprotective agent is one of dimethyl sulfoxide, glycerol, propylene glycol, ethylene glycol, propanediol, or a combination thereof.

\* \* \* \* \*